United States Patent
Madison

(10) Patent No.: US 8,247,405 B2
(45) Date of Patent: Aug. 21, 2012

(54) SKIN LIGHTENING COMPOSITIONS WITH ACETYLCHOLINESTERASE INHIBITORS

(75) Inventor: Stephen Alan Madison, Newtown, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 498 days.

(21) Appl. No.: 12/332,002

(22) Filed: Dec. 10, 2008

(65) Prior Publication Data

US 2010/0143277 A1 Jun. 10, 2010

(51) Int. Cl.
*A61K 31/55* (2006.01)

(52) U.S. Cl. .................. 514/215; 514/558; 424/401

(58) Field of Classification Search .................. None
See application file for complete search history.

(56) References Cited

U.S. PATENT DOCUMENTS

| | | | |
|---|---|---|---|
| 2,701,225 A | 2/1955 | Lorenz | |
| 4,895,841 A | 1/1990 | Sugimoto et al. | |
| 4,948,807 A | 8/1990 | Rosin et al. | |
| 5,538,984 A | 7/1996 | Villalobos et al. | |
| 5,998,423 A | 12/1999 | Manneth et al. | |
| 6,875,425 B2 | 4/2005 | Harichian et al. | |
| 7,247,294 B1 | 7/2007 | Shore et al. | |
| 7,250,158 B1 | 7/2007 | Shore et al. | |
| 7,270,805 B1 | 9/2007 | Shore et al. | |
| 2002/0192243 A1* | 12/2002 | Hsu et al. | 424/400 |
| 2004/0253275 A1* | 12/2004 | Eini et al. | 424/400 |

OTHER PUBLICATIONS

Loizzo et al., Natural Products and their Derivatives as Cholinesterase Inhibitors in the Treatment of Neurodegenerative Disorders: An Update; *Current Medicinal Chemistry*, 2008, 15, pp. 1209-1228.

Co-pending application for: Applicant—Madison; U.S. Appl. No. 12/141,561, filed Jun. 18, 2008, entitled Compositions for Lightening Skin Color.

Co-pending application for: Applicant—Madison; U.S. Appl. No. 12/185,885, filed Aug. 5, 2008, entitled Skin Lightening Compositions Comprising $CO_2$ Extracts.

Co-pending application for: Applicant—Ghatlia et al.; U.S. Appl. No. 12/004,572, filed Dec. 21, 2007; entitled Topical Composition Comprising Coloring Antioxidants.

* cited by examiner

*Primary Examiner* — David J Blanchard
*Assistant Examiner* — Barbara Frazier
(74) *Attorney, Agent, or Firm* — Edward A. Squillante, Jr.

(57) ABSTRACT

Skin lightening additives and skin lightening compositions having an acetylcholinesterase inhibitor are described. The compositions are suitable for topical application and may comprise inhibitors like galanthamine, taspine or both.

3 Claims, No Drawings

SKIN LIGHTENING COMPOSITIONS WITH ACETYLCHOLINESTERASE INHIBITORS

FIELD OF THE INVENTION

The present invention is directed to a skin lightening additive as well as a composition comprising the same. More particularly, the present invention is directed to a cosmetic composition comprising a skin lightening additive whereby the skin lightening additive comprises an acetylcholinesterase inhibitor. The skin lightening additive, when used in a cosmetic composition, results in a composition that can surprisingly provide skin lightening benefits to consumers using the same.

BACKGROUND OF THE INVENTION

Many consumers are concerned with the characteristics of their skin. For example, consumers are concerned with the degree of pigmentation of their skin, freckles and/or age spots. Other consumers wish to reduce skin darkening caused by exposure to sunlight. To meet the needs of consumers, many attempts have been made to develop products that improve skin characteristics. The products developed thus far, however, often tend to have low efficacy, undesirable side effects or both.

There is an increasing interest to develop a cosmetic composition that comprises new skin lightening additives. This invention, therefore, is directed to cosmetic compositions that comprise new skin lightening additives. The cosmetic compositions of the present invention preferably comprise, as a lightening additive, an acetylcholinesterase inhibitor. The cosmetic compositions of this invention can surprisingly result in skin lightening after being topically applied.

ADDITIONAL INFORMATION

Efforts have been disclosed for making skin care cosmetic compositions. In U.S. Pat. No. 6,875,425, skin lightening agents with 4-substituted resorcinol derivative compounds are described.

Other efforts have been disclosed for making skin treatment compositions. In U.S. Pat. Nos. 7,250,158 and 7,247,294, methods for treating with skin lightening agents are described.

Still other efforts have been disclosed for treating skin. In U.S. Pat. No. 5,998,423, compositions with polycyclic nitrogen heterocycles are described.

Even other efforts have been disclosed that employ acetylcholinesterase inhibitors. In U.S. Pat. Nos. 2,701,225, 4,895,841, 4,948,807 and 5,538,984, the use of acetylcholinesterase inhibitors is described.

None of the additional information above describes skin lightening compositions that comprise, as a lightening additive, an acetylcholinesterase inhibitor.

SUMMARY OF THE INVENTION

In a first aspect, the present invention is directed to a skin lightening additive, the skin lightening agent comprising an acetylcholinesterase inhibitor.

In a second aspect, the present invention is directed to a cosmetic composition for skin lightening, the cosmetic composition comprising a skin lightening agent comprising the skin lightening additive of the first aspect of this invention.

In a third aspect, the present invention is directed to a method for lightening skin with the cosmetic composition of the second aspect of this invention.

All other aspects of the present invention will more readily become apparent upon considering the detailed description and examples which follow.

Cosmetic composition, as used herein, is meant to include a composition for topical application to skin of mammals, especially humans. Such a composition may be generally classified as leave-on or rinse off, and is meant to include conditioners or tonics, lipsticks, color cosmetics, and general topical compositions that in some fashion and at the very least, reduce the effect of melanin on keratinocytes. Lightening and whitening as used herein are meant to mean the same and they include the lightening of skin directly as well as the lightening of spots on the skin, like age spots and freckles. Skin lightening agent means a component suitable to result in physical, but especially biological whitening (i.e., a reduction in melanin production) whereby the skin lightening agent can comprise, consist essentially of or consist of the skin lightening additive, and therefore, can also contain a skin lightening source. Comprising, as used herein, is meant to include consisting essentially of and consisting of.

The cosmetic composition of the present invention can be in the form of a liquid, lotion, cream, serum, gel, soap bar or toner, or applied via a face mask or patch. The composition of this invention is one that at the very least, lightens skin when skin is meant to include skin on the face, neck, chest, back, arms, buttocks, hands, legs and scalp. All ranges identified herein are meant to implicitly include all ranges subsumed therein, if, for example, reference to the same is not explicitly made.

DETAILED DESCRIPTION OF THE PREFERRED EMBODIMENTS

The only limitation with respect to the skin lightening additive that may be used in this invention is that the same may be employed in a topical composition suitable for use on humans. The preferred additive used in this invention is an acetylcholinesterase inhibitor.

Illustrative and often preferred skin lightening additives (i.e., acetylcholinesterase inhibitors) suitable for use in the present invention are represented as compounds having the formulae:

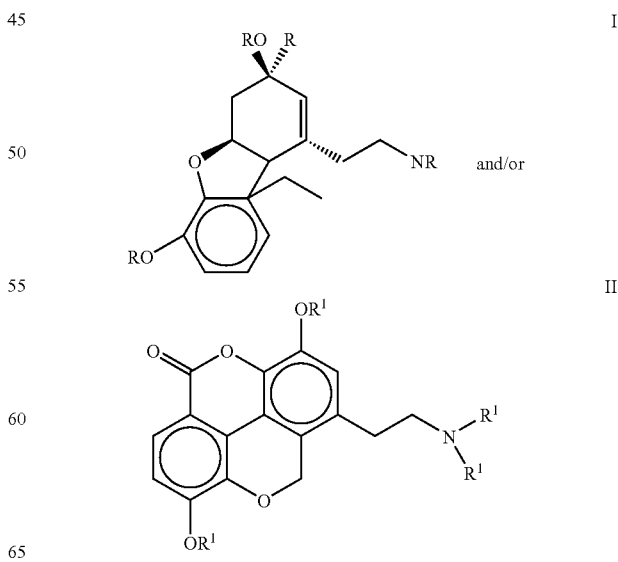

wherein:

each R is independently H or a $C_1$-$C_6$ linear, branched or cyclic alkyl, and each $R^1$ is independently H, a $C_1$-$C_6$ linear, branched or cyclic alkyl, a $C_2$-$C_6$ alkenyl, or aryl.

Other illustrative yet non-limiting examples of skin lightening additives suitable for use in this invention include lawsaritol, phenserine, corydaline, physostigmine, tacrine, icopezil, donepezil, rivastigmine, metrifonate, schisandrol B, gomisin A, gomisin C, gomisin D, gomisin G, ensaculin, linarin, huperazine A, huperine X, huperine Y, O-acetyllycorine, and luteidine. To the extent any neutralized derivatives of the acetylcholinesterase inhibitors exist, such derivatives (e.g., salts thereof) may be employed in this invention. Illustrative salts include ammonium sulfate, phosphate and carbonate salts as well as ammonium halide salts and mixtures thereof.

It is within the scope of the present invention to employ a skin lightening additive or mixture of additives in the skin lightening agent of the desired cosmetic composition. In an especially preferred embodiment, the skin lightening additive used is galanthamine (represented formula I), taspine (represented by formula II) or mixtures thereof.

Typically, the skin lightening additive makes up from about 25 to about 100%, and preferably, from about 50 to about 100%, and most preferably, from about 75 to about 100% by weight of the skin lightening agent, and including all ranges subsumed therein. Moreover, the skin lightening additive of this invention typically makes up from about 0.01 to about 15%, and preferably, from about 0.1 to about 10%, and most preferably, from about 0.5 to about 6% by weight of the cosmetic composition, based on total weight of the cosmetic composition and including all ranges subsumed therein. The skin lightening agent typically makes up from about 0.0025 to about 15% by weight of the cosmetic composition, based on total weight of the cosmetic composition and including all ranges subsumed therein.

The acetylcholinesterase inhibitors that may be used in this invention may be obtained from suppliers like Indofine Chemical Company, Rubamin Limited as well as Sigma Aldrich. Such inhibitors are typically natural products isolated from plants.

It should be known that commercially acceptable and conventional vehicles may be used, acting as diluents, dispersants and/or carriers for the skin lightening agents and additives described herein and for any other optional but often preferred ingredients. Therefore, the cosmetically acceptable vehicle suitable for use in this invention may be aqueous-based, anhydrous or an emulsion whereby a water-in-oil or oil-in-water emulsion is generally preferred. If the use of water is desired, water typically makes up the balance of the cosmetic composition, and preferably, makes up from about 5 to about 99%, and most preferably, from about 40 to about 80% by weight of the cosmetic composition, including all ranges subsumed therein.

In addition to water, organic solvents may be optionally included to act as carriers or to assist carriers within the cosmetic compositions of the present invention. Illustrative and non-limiting examples of the types of organic solvents suitable for use in the present invention include alkanols like ethyl and isopropyl alcohol, mixtures thereof or the like.

Other optional additives suitable for use include ester oils like isopropyl myristate, cetyl myristate, 2-octyldodecyl myristate, avocado oil, almond oil, olive oil, neopentylglycol dicaprate, mixtures thereof or the like. Typically, such ester oils assist in emulsifying the cosmetic composition of this invention, and an effective amount is often used to yield a stable, and most preferably, water-in-oil emulsion.

Emollients may also be used, if desired, as carriers within the cosmetic composition of the present invention. Alcohols like 1-hexadecanol (i.e., cetyl alcohol) are often desired as are the emollients generally classified as silicone oils and synthetic esters. Silicone oils suitable for use include cyclic or linear polydimethylsiloxanes containing from 3 to 9, preferably from 4 to 5, silicon atoms. Nonvolatile silicone oils useful as an emollient material in the inventive cosmetic composition described herein include polyalkyl siloxanes, polyalkylaryl siloxanes and polyether siloxane copolymers. The essentially non-volatile polyalkyl siloxanes useful herein include, for example, polydimethylsiloxanes.

The ester emollients that may optionally be used are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono-and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, stearyl stearate and arachidyl behenate.

(5) Sterols esters, of which cholesterol fatty acid esters are examples.

Emollients when used, typically make up from about 0.1 to about 50% by weight of the cosmetic composition, including all ranges subsumed therein.

Fatty acids having from 10 to 30 carbon atoms may also be included as cosmetically acceptable carriers within the composition of the present invention. Illustrative examples of such fatty acids include pelargonic, lauric, myristic, palmitic, stearic, isostearic, oleic, linoleic, arachidic, behenic or erucic acid, and mixtures thereof. Compounds that are believed to enhance skin penetration, like dimethyl sulfoxide, may also be used as an optional carrier.

Humectants of the polyhydric alcohol type may also be employed in the cosmetic compositions of this invention. The humectant often aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.2 to 25%, and preferably, from about 0.5 to about 15% by weight of the cosmetic composition, based on total weight of the cosmetic composition and including all ranges subsumed therein.

Thickeners may also be utilized as part of the cosmetically acceptable carrier in the cosmetic compositions of the present invention. Typical thickeners include cross-linked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0 to 5%, usually from 0.001 to 1%, optimally from 0.01 to 0.5% by weight.

Collectively, the water, solvents, silicones, esters, fatty acids, humectants and/or thickeners will constitute the cosmetically acceptable carrier in amounts from 1 to 99.9%, preferably from 80 to 99% by weight.

Surfactants may also be present in cosmetic compositions of the present invention. Total concentration of the surfactant will range from about 0 to about 40%, and preferably, from about 0 to about 20%, optimally from about 0 to about 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; mono- and di-fatty acid esters of ethylene glycol; fatty acid monoglyceride; sorbitan, mono- and di-$C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, acyl glutamates, $C_8$-$C_{20}$ alkyl ether phosphates and combinations thereof.

Perfumes may be used in the cosmetic composition of this invention. Illustrative non-limiting examples of the types of perfumes that may be used include those comprising terpenes and terpene derivatives like those described in Bauer, K., et al., *Common Fragrance and Flavor Materials*, VCH Publishers (1990).

Illustrative yet non-limiting examples of the types of fragrances that may be used in this invention include myrcene, dihydromyrenol, citral, tagetone, cis-geranic acid, citronellic acid, mixtures thereof or the like.

Preferably, the amount of fragrance employed in the cosmetic composition of this invention is in the range from about 0.0% to about 10%, more preferably, about 0.00001% to about 5 wt %, most preferably, about 0.0001% to about 2%.

Various types of optional additional active ingredients may be used in the cosmetic compositions of the present invention. Actives are defined as skin benefit agents other than emollients and other than ingredients that merely improve the physical characteristics of the composition. Although not limited to this category, general examples include talcs and silicas, as well as alpha-hydroxy acids, beta-hydroxy acids, zinc salts, and sunscreens.

Beta-hydroxy acids include salicylic acid, for example. Zinc pyrithione is an example of the zinc salts useful in the cosmetic composition of the present invention.

Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation. Additives that reflect or scatter the suns rays may also be employed. These additives include oxides like zinc oxide and titanium dioxide.

Many cosmetic compositions, especially those containing water, should be protected against the growth of potentially harmful microorganisms. Anti-microbial compounds, such as triclosan, and preservatives are, therefore, typically necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the cosmetic composition.

Still other optional ingredients that may be used with the cosmetic composition of this invention include dioic acids (e.g., malonic acid, sebacic acid), antioxidants like vitamin E, retinoids, including retinoic acid, retinal, retinol and retinyl esters, conjugated linoleic acid, petroselinic acid and mixtures thereof, as well as any other conventional ingredients well known for wrinkle-reducing, anti-acne effects and reducing the impact of sebum.

Even other optional ingredients that may be employed in the cosmetic composition of the present invention are skin lightening sources in addition to the skin lightening additive described in this invention. Illustrative yet non-limiting examples of skin lightening sources that may be used along with the skin lightening additives of this invention are niacinamide, vitamin C and its derivatives, 12-hydroxystearic acid, resorcinols and their derivatives (including those esterified with, for example, ferulic acid, vanillic acid or the like), extracts of kudzu, chamomile, and yarrow as well as any mixtures of the skin lightening sources in addition to skin lightening additive.

The cosmetic compositions of the present invention are intended for use primarily as a product for topical application to human skin, especially and at least as a product for lightening the skin. Thus, the inventor has discovered that the described additives unexpectedly have skin lightening capabilities whereby the same may be employed as skin lightening additives in topical cosmetic compositions that are applied to areas of the skin where lightening or whitening is desired. Other benefits from using the cosmetic composition of this invention may include skin moisturizing, decreasing the effect of sebum on the skin and skin wrinkle reducing. Often, the cosmetic composition of the present invention has a melting point from about 30° C. to about 45° C., including all ranges subsumed therein. In an especially preferred embodiment, the cosmetic composition of the present invention has a pH from about 4.5 to about 7.5, including all ranges subsumed therein.

When making the cosmetic composition of the present invention, the desired ingredients are mixed in no particular order and usually at temperatures from about 70 to about 80° C. and under atmospheric pressure.

The packaging for the composition of this invention can be a patch, bottle, tube, roll-ball applicator, propellant driven aerosol device, squeeze container or lidded jar.

The examples which follow are provided to illustrate and facilitate an understanding of the invention. The examples are not intended to limit the scope of the claims.

EXAMPLE

Experiment:

Monolayer cultures were initiated from cryopreserved cultures of human epidermal melanocytes from dark human neonatal foreskin (HEMn-DP; C-202-5C; Cascade Biologics™), according to the manufacturer's instructions. Cells were cultured in Medium 254 (M-254-500, Cascade Biologics) supplemented with Human Melanocyte Growth Supplement (HMGS; S-0002-5, Cascade Biologics). Stocks of these cultures were generated and stored in Sythn-a-Freeze® cryopreservation media (R-005-50. Cascade Biologics) in liquid nitrogen at passage 2.

For use in assays, cells were thawed according to manufacturer's instructions, and subcultured to increase cell numbers as required. Cells were then plated into 6-well plates at ~200,000 cells per well and incubated at 37° C., 5% $CO_2$, and were used in assays at passage 4.

Once the melanocytes had adhered to the 6-well plate's (approx. 4-6 hr.), the medium was replaced with Medium 254 containing Human Melanocyte Growth Supplement PMA-free (HMGS-2; S-016-5 hereafter termed depleted media) for approximately 16 hours, or overnight, prior to treatment with the actives.

Development of Screening Assay

To develop the screening assay a variety of cell concentrations and incubation times were tested to obtain optimized measurable levels of melanin. During this process no materials were applied to the cells. In addition a standard melanin (M8631, Sigma Aldrich) stock solution was prepared in Solvable™ reagent (5NE9100, Perkin Elmer) to obtain a standard curve for evaluating levels of melanin extracted from cells using a spectrophotometer. Method development was performed to obtain the optimum time required to solubilize the melanin into solution without degradation and a reduction in color.

Addition of Test Solutions

All stocks of active materials were diluted in DMSO, ethanol or media, before further dilution in depleted media. Treatments were applied to the cells in 6-well plates in triplicate for 72 hours after which time the cells were harvested. Appropriate solvent controls in triplicate were incorporated into each assay.

Harvesting of Cells and Preparation of Cell Lysate

After 72 hours, media was removed form the cells and the cells were washed once in Dulbecco's PBS. The PBS wash was removed and discarded and care being taken to ensure that all excess PBS was removed as far as possible. 1 mL trypsin-EDTA solution (R-001-100, Cascade Biologic™) was added and cells incubated at room temperature for ~1 minute. Microscopic observation was carried out to ensure all cells had detached from the plate. The resulting cell suspension was transferred to a 1.5 mL Eppendorf tube, 50 μL was removed for a cell count (Beckman coulter counter), and the remaining suspension was centrifuged at 13,000 rpm for 5 minutes. The supernatant was discarded and the cell pellets were frozen at −20° C.

Quantification of Total Melanin

The cell pellets were thawed at room temperature, and each pellet was re-suspended in 75 μL Solvable™ reagent (6NE9100, Perkin Elmer). Each tube was vortexed briefly, before incubating in a water bath at 60° C. for 1 hour. After the 1 hour incubation, each tube was vortexed and then centrifuged at 13,000 rpm for 15 minutes. The supernatant containing the extracted melanin was transferred to a 96 well plate and the absorbance at 490 nm recorded on a Dynex MRX-II plate reader.

Statistical Analyses of Data

Each ingredient was tested in triplicate and compared against the relevant vehicle control. The total amount of melanin extracted was calculated from a melanin standard curve. All resultant data was normalized to the total number of the cells in the sample. Data was subjected to the F-test for variance, followed by Student's t-test (assuming equal or unequal variance depending on results of the F-test.

TABLE

| Treatment | Amount | mg melanin/100K cells | Mean mg melanin/100K cells |
|---|---|---|---|
| Water vehicle* | 1 μL | 26.5 | 27.4$^a$ |
| Water vehicle* | 1 μL | 26.1 | |
| Water vehicle* | 1 μL | 29.4 | |
| Untreated* | — | 25.6 | 25.0$^b$ |
| Untreated* | — | 24.4 | |
| Galanthamine | 10 μM | 23.3 | 23.4$^c$ |
| Galanthamine | 10 μM | 23.7 | |
| Galanthamine | 10 μM | 23.0 | |
| Galanthamine | 1 μM | 21.0 | 19.4$^d$ |
| Galanthamine | 1 μM | 18.6 | |
| Galanthamine | 1 μM | 18.5 | |
| Galanthamine | 0.1 μM | 21.2 | 24.0$^e$ |
| Galanthamine | 0.1 μM | 26.7 | |
| Galanthamine | 0.1 μM | 23.9 | |

*control
$^a$means for water vehicle treatment;
$^b$means for untreated;
$^{c,d}$and$^e$means for galanthamine treatment at 10 μM, 1 μM and 0.1 μM, respectively.

The data in the Table unexpectedly shows that use of an acetylcholinesterase inhibitor results in a decrease in melanin production in cultured cells.

What is claimed is:

1. A method for lightening skin comprising the step of identifying skin where lightening or whitening is desired and topically applying to the skin a cosmetic composition comprising:
    (a) a skin lightening agent consisting essentially of a skin lightening additive which is galanthamine or a salt thereof;
    (b) a cosmetically acceptable carrier; and
    (c) 12-hydroxystearic acid, to lighten or whiten the skin.

2. The method for lightening skin according to claim 1 wherein the cosmetic composition further comprises antioxidants, conjugated linoleic acid, petroselinic acid, alpha- and/or beta-hydroxy acids, a retinoid or mixtures thereof.

3. The method for lightening skin according to claim 1 wherein the cosmetic composition further comprises niacinamide.

* * * * *